(12) United States Patent
Otinger

(10) Patent No.: US 7,744,043 B2
(45) Date of Patent: Jun. 29, 2010

(54) CPAP HOSE TENDER

(76) Inventor: Sam J. Otinger, 1242 Alabama Hwy. 205 South, Boaz, AL (US) 35956

( * ) Notice: Subject to any disclaimer, the term of this patent is extended or adjusted under 35 U.S.C. 154(b) by 0 days.

(21) Appl. No.: 12/606,697

(22) Filed: Oct. 27, 2009

(65) Prior Publication Data

US 2010/0102176 A1 Apr. 29, 2010

Related U.S. Application Data

(63) Continuation-in-part of application No. 12/284,596, filed on Sep. 24, 2008, now abandoned.

(51) Int. Cl.
*A62C 13/76* (2006.01)

(52) U.S. Cl. ............... 248/75; 248/72; 248/79; 248/226.11

(58) Field of Classification Search ............ 248/59, 248/75, 226.11, 228.4, 229.23, 229.13, 103, 248/79, 77, 72
See application file for complete search history.

(56) References Cited

U.S. PATENT DOCUMENTS

| | | | | |
|---|---|---|---|---|
| 1,786,459 A | * | 12/1930 | Simons | 248/104 |
| 2,696,963 A | * | 12/1954 | Shepherd | 248/229.15 |
| 2,963,247 A | * | 12/1960 | Collier et al. | 248/81 |
| 4,666,111 A | * | 5/1987 | Schuler | 248/125.1 |
| 4,979,703 A | * | 12/1990 | Fleming | 248/65 |
| 6,224,027 B1 | * | 5/2001 | Johnson et al. | 248/125.8 |
| 6,854,694 B1 | * | 2/2005 | Van Etten | 248/75 |
| 7,040,581 B2 | * | 5/2006 | Noelke et al. | 248/75 |
| 2004/0089778 A1 | * | 5/2004 | Valentine et al. | 248/229.13 |
| 2005/0230580 A1 | * | 10/2005 | Bryan et al. | 248/226.11 |
| 2007/0045481 A1 | * | 3/2007 | Adams | 248/59 |

* cited by examiner

*Primary Examiner*—J. Allen Shriver, II
*Assistant Examiner*—Bradley H Duckworth
(74) *Attorney, Agent, or Firm*—Welsh & Flaxman LLC

(57) ABSTRACT

A hose tender is provided for use with a CPAP system. The CPAP system includes a breathing mask connected to a CPAP air generator via a hose. The hose tender supports the hose above a user in a convenient and safe manner. The hose tender includes a support arm including a first end and second end. The first end of the support arm is provided with an arcuate coupling portion and the second end is provided with a hose engaging portion. The hose engaging portion includes a cantilevered section secured to the second end of the support arm such that a longitudinal axis of the cantilevered section is oriented substantially perpendicular to a longitudinal axis of the support arm; wherein the cantilevered section includes an abutment member and a return portion with an horizontal line member connected therebetween. The hose tender also includes a clamp for selectively securing the support arm to a support surface. The clamp includes an upper support arm receiving hole and a lower support arm receiving hole and the arcuate coupling portion is shaped and dimensioned to simultaneously extend through both the upper support arm receiving hole and the lower support arm receiving hole. The clamp further includes a spring having coils and the arcuate coupling portion of the support arm is shaped and dimensioned to seat within recesses defined by the coils of the spring.

20 Claims, 5 Drawing Sheets

CPAP HOSE TENDER

CROSS REFERENCE TO RELATED APPLICATIONS

This application is a continuation-in-part of U.S. patent application Ser. No. 12/284,596, entitled "CPAP Hose Tender", filed Sep. 24, 2008 now abandoned.

BACKGROUND OF THE INVENTION

1. Field of the Invention

This invention relates to a medical device, more particularly, a medical device managing and tending the hose of a continuous positive air pressure system (CPAP) to aide and comfort the CPAP users. More particularly, the present invention relates to the field of breathing by tending to the CPAP air hose running from the sleep apnea patient's face mask to the CPAP machine and allowing for free side to side, and up and down, movement of the hose thereby resulting in rested sleep.

2. Description of the Related Art

Many CPAP users have difficulty sleeping while using a CPAP machine. Previous devices for aiding the hose management of CPAP users are ridged, difficult to use, not flexible and do not address, in particular, the CPAP patient hose management. However, the aggravation associated with currently available devices may cause users to use the CPAP machine less frequently than they otherwise would. Limited use of the CPAP machine could result in serious medical problems.

As briefly discussed above, currently available devices for tending to the air hose of a CPAP machine are simply inadequate. The inventor is a sleep apnea patient and has suffered from hose management problems associated with the use of his CPAP machine. In self defense the inventor of the present CPAP hose tender developed a device for tending to a hose of a CPAP machine. Much of the innovation associated with the development of the present CPAP hose tender is based upon the inventor's experience from his Navy days tending the hose while fueling ships.

As those skilled in the art will certainly appreciate, sleep apnea affects a large percentage of the population and leads to severe medical problems from lack of sleep, oxygen depravation and other medical complications. The common treatment prescribed is the use of the CPAP machine. A CPAP machine commonly includes a breathing mask worn by the patient. The breathing mask is connected to a hose connected to a CPAP air generator. Positive pressure air from the CPAP air generator is delivered to the breathing mask via the air hose. The hose creates huge discomfort for the user. After attaching the hose to the facemask, movement of the user is restricted because the hose commonly drags across the bed covers and puts additional pressure on the facemask. This additional pressure breaks the seal securing the breathing mask about the mouth and nose of the user, and ultimately results in awakening the patient from sleep.

According to the present invention, disadvantages and problems associated with previous devices and methods have been overcome. The CPAP hose tender of the present invention effectively aids the patient's air hose management. In accordance with one embodiment of the present invention, the apparatus comes fully assembled and ready for the CPAP user to begin use without the aide of complex instruction. In addition, no bolts or screws are needed for attachment of the present invention. The present device is lightweight and no assistance is needed to install the CPAP hose tender. One need only clamp the present CPAP hose tender on a headboard or other support. The apparatus offers ease of use and CPAP user's life need not be interrupted as the CPAP hose tender is easy to travel with.

An important technical advantage of the present invention is that the stainless steel rod is economical to manufacture and comes from stock material. In addition, the clamp also comes from stock material. Another important technical advantage of the present invention is the comfort provided to the user. Also, the CPAP users are allowed free movement from side to side and up and down while using their CPAP machines, therefore, increasing the use of the CPAP as prescribed.

SUMMARY OF THE INVENTION

It is, therefore, an object of the present invention to provide a hose tender for use with a CPAP system. The CPAP system includes a breathing mask connected to a CPAP air generator via a hose. The hose tender supports the hose above a user in a convenient and safe manner. The hose tender includes a support arm including a first end and second end. The first end of the support arm is provided with an arcuate coupling portion. A hose engaging portion extends from the support arm. The hose engaging portion includes a cantilevered section secured to the second end of the support arm such that a longitudinal axis of the cantilevered section is oriented substantially perpendicular to a longitudinal axis of the support arm, wherein the cantilevered section includes an abutment member connected to an horizontal line member. The hose tender also includes a clamp for selectively securing the support arm to a support surface. The clamp includes an upper support arm receiving hole and a lower support arm receiving hole and the arcuate coupling portion is shaped and dimensioned to simultaneously extend through both the upper support arm receiving hole and the lower support arm receiving hole. The clamp further includes a spring having coils and the arcuate coupling portion of the support arm is shaped and dimensioned to seat within recesses defined by the coils of the spring.

It is also an object of the present invention to provide a hose tender wherein the clamp includes a first clamp member and a second clamp member, and the first clamp member and the second clamp member are pivotally connected at central pivot point which substantially bisects each of the first clamp member and the second clamp member.

It is another object of the present invention to provide a hose tender wherein the first clamp member includes a first clamp member upper portion and a first clamp member lower portion with a pivot protrusion extending laterally along a length of the first clamp member. The second clamp member includes a second clamp member upper portion and a second clamp member lower portion with a pivot protrusion extending laterally along a length of the second clamp member.

It is a further object of the present invention to provide a hose tender wherein the spring is coupled to the first clamp member and the second clamp member adjacent a pivot pin for biasing the clamp to a closed orientation where the first clamp member lower portion and the second clamp member lower portion are biased toward each other and the first clamp member upper portion and the second clamp member upper portion are biased away from each other.

It is also an object of the present invention to provide a hose tender wherein the second clamp member upper portion includes the upper support arm receiving hole and the second clamp member lower portion includes the lower support arm receiving hole.

It is another object of the present invention to provide a hose tender wherein the lower support arm receiving hole and the upper support arm receiving hole are oriented to extend substantially transversely to a longitudinal axis of the second clamp member.

It is a further object of the present invention to provide a hose tender wherein the abutment member is a 180-degree turn at a connection of the support arm to the cantilevered section.

It is also an object of the present invention to provide a hose tender wherein the abutment member includes a vertically oriented first leg connected directly to the support arm, a vertically oriented second leg and a connecting member extending between the vertically oriented first leg and the vertically oriented second leg.

It is another object of the present invention to provide a hose tender wherein the horizontal line member extends from the abutment member to a return portion of the cantilevered section.

It is a further object of the present invention to provide a hose tender wherein the return portion of the cantilevered section includes a first member aligned with and extending from the horizontal line member, a second member oriented substantially perpendicular to the first member, and an arcuate third member that completes the return created by the return portion.

It is also an object of the present invention to provide a hose tender wherein the return portion further includes a return arm that extends from the arcuate third member.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

Figure 1:
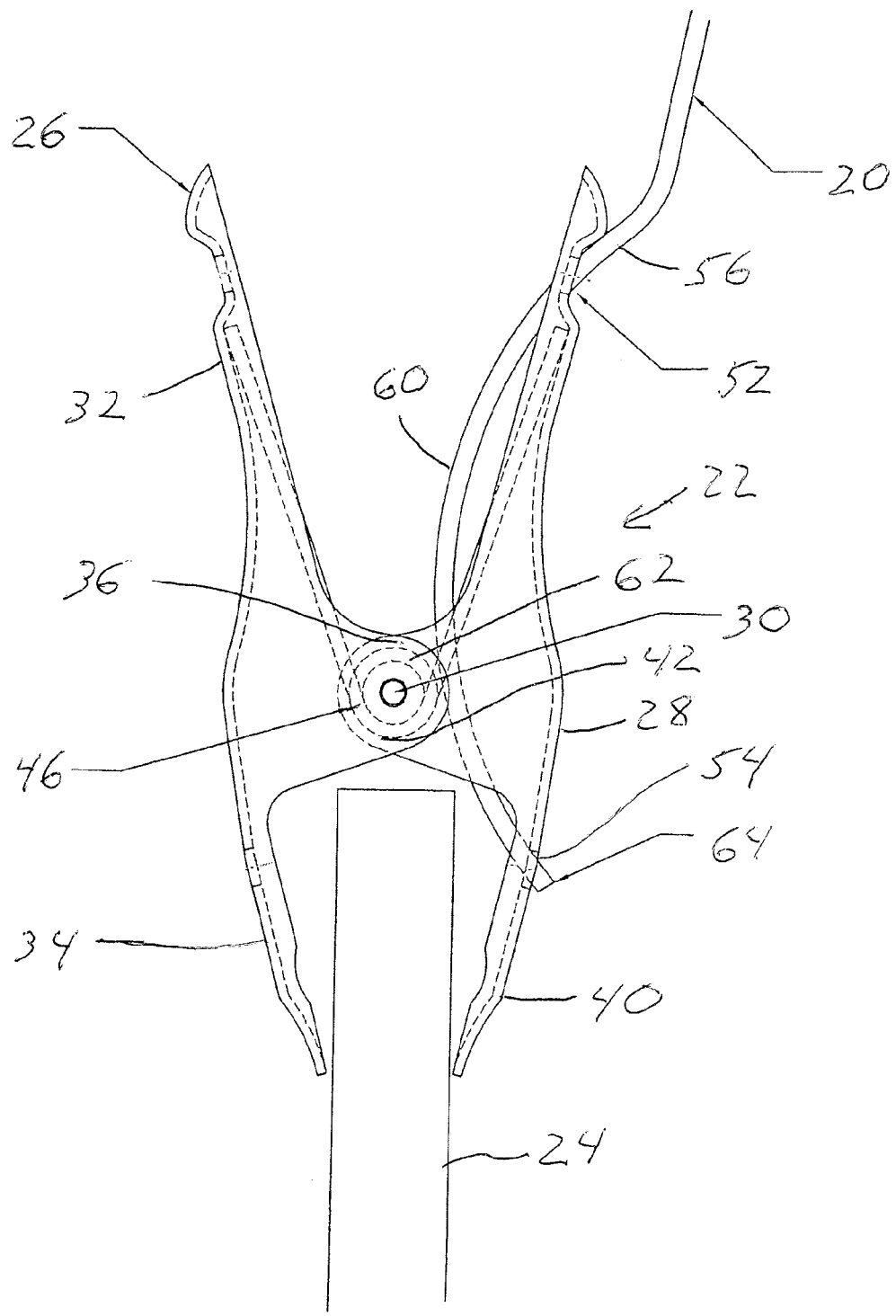
FIG. 1 is a front view of the C-clamp.
Figure 1A:
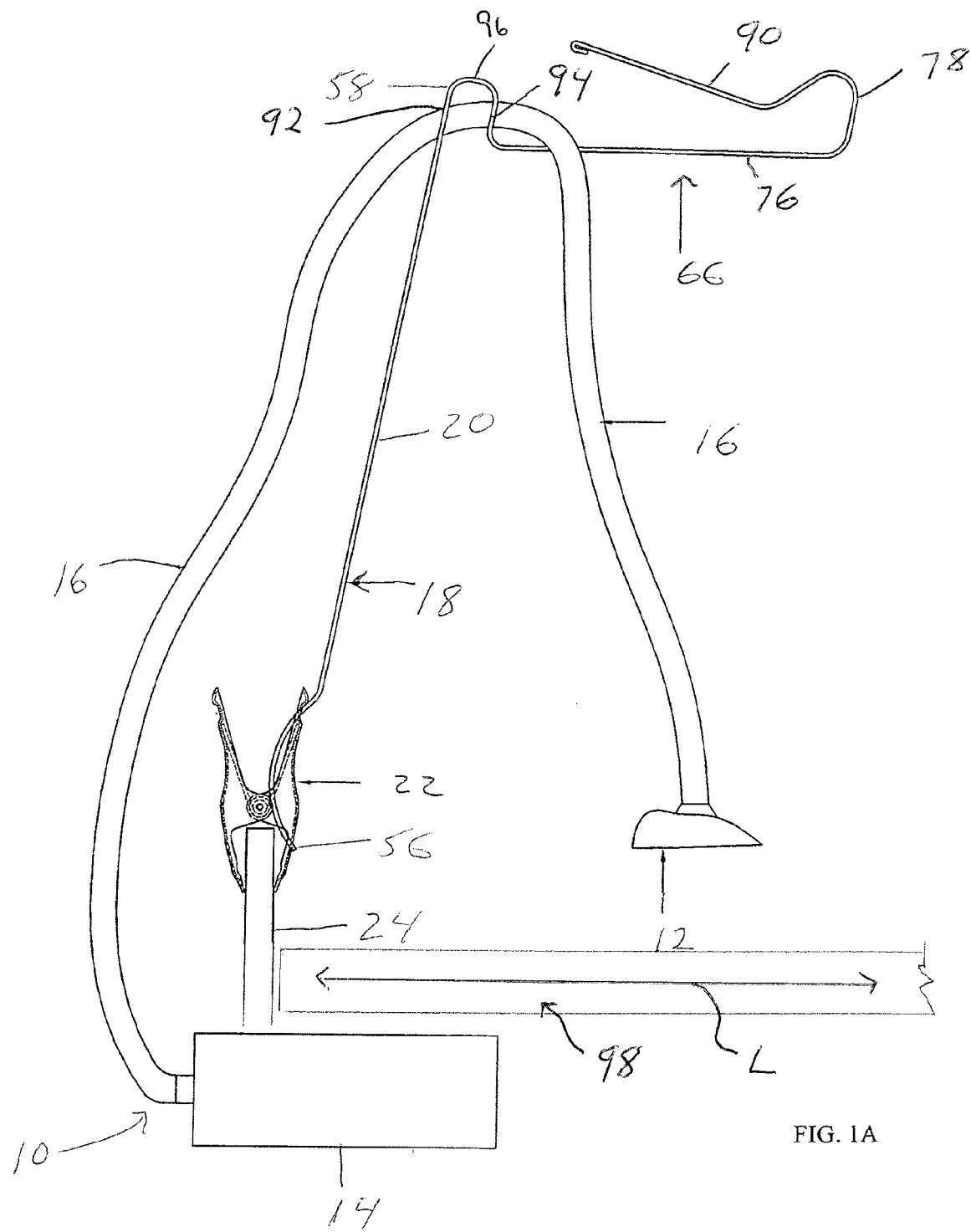
FIG. 1A is a perspective view of the CPAP hose tender.

In accordance with the present invention, and with reference to FIG. 1A, a CPAP system 10 is shown with the breathing mask 12 is shown connected to the CPAP air generator 14 via an air hose 16 supported by the present CPAP hose tender 18. As will be appreciated based upon the following disclosure, the present CPAP hose tender 18 is flexible and will accept a variety of hose sizes (diameters and lengths) used by CPAP system 10. As a result, the present CPAP hose tender 18 offers great flexibility and allows for free patient movement without interference from the air hose 16.

Briefly, and with reference to FIGS. 1 to 4, the present CPAP hose tender 18 includes a support arm 20, a hose engaging portion 66 extending from the support arm 20, and a clamp 22 for selectively securing the support arm 20 to a support surface 24, for example, the frame (in particular, the headboard, of a bed 98). In accordance with a preferred embodiment of the present invention, the support arm 20 and hose engaging portion 66 are formed form a ⅛ inch diameter stainless steel rod, although it is contemplated the support arm 20 and air hose engaging portion 66 may be made out of other materials without departing from the spirit of the present invention. In addition, and with reference to the various figures, it should be apparent that support arm 20 and the air hose engaging portion 66 are oriented to lie in a single plane.

More particularly, and with reference to FIG. 1, a clamp 22 in accordance with a preferred embodiment of the present invention is shown. In accordance with a preferred embodiment, the clamp 22 is a 6 inch C-clamp. The clamp 22 includes a first clamp member 26 (that is, the left portion of the clamp) and a second clamp member 28 (that is the right portion of the clamp). The first and second clamp members 26, 28 are pivotally connected at central pivot point 30 which substantially bisects each of the first and second clamp members 26, 28. As such, the first clamp member 26 includes a first clamp member upper portion 32 and a first clamp member lower portion 34 with a pivot protrusion 36 extending lateral along the length of the first clamp member 26.

Similarly, the second clamp member 28 includes a second clamp member upper portion 38 and a second clamp member lower portion 40 with a pivot protrusion 42 extending lateral along the length of the second clamp member 28 between the upper portion and the lower portion. As such, a pivot pin 44 pivotally secures the pivot protrusion 36 of the first clamp member 26 to the pivot protrusion 42 of the second clamp member 28. In accordance with a preferred embodiment, the pivot pin 44 is a rivet which holds the first and second clamp members 26, 28 together in a pivotal arrangement.

A spring 46 formed of several coils 62 is coupled to the first clamp member 26 and the second clamp member 28 adjacent the pivot pin 44 for biasing the clamp 22 to a closed orientation where the lower portions 34, 40 of the first and second clamp members 26, 28 are biased toward each other and the upper portions 32, 38 of the first and second clamp members 26, 28 are biased away from each other. When one wishes to release the clamp 22 from a support surface 24 to which it is secured, the user need only apply pressure to the upper portions 32, 38 of the first and second clamp members 26, 28 moving the upper portions 32, 38 of the first and second clamp members 26, 28 toward each other thereby moving the lower portions 34, 40 of the first and second clamp members 26, 28 away from each other.

Attachment of the support arm 20, and ultimately the hose engaging portion 66, to the clamp 22 is facilitated by the provision of support arm holes in the upper portion 38 and the lower portion 40 of the second clamp member 28. In particular, the upper portion 38 of the second clamp member 28 (that is, the right upper portion of the clamp) is provide with an upper support arm receiving hole 52 and the lower portion 40 of the second clamp member 28 is provided with a lower support arm receiving hole 54. The lower support arm receiving hole 54 and the upper support arm receiving hole 52 are oriented to extended substantially transversely to the longitudinal axis of the second clamp member 28.

As discussed above, the present CPAP air hose tender 18 includes a support arm 20 with an air hose engaging portion 66 extending therefrom. The support arm 20 includes a first end 56 and a second end 58. The first end 56 is shaped and dimensioned for coupling to the second clamp member 28 via the upper and lower support arm receiving holes 52, 54. As such, the first end 56 of the support arm 20 is provided with an arcuate coupling portion 60 shaped and dimensioned to simultaneously extend through both the upper support arm receiving hole 52 and the lower support arm receiving hole 54 of the right clamp member 28. The arcuate coupling portion 60 of the first end 56 of the support arm 20 is shaped and dimensioned to extend through both the upper support arm receiving hole 52 and the lower support arm receiving hole 54 of the right clamp member 28 in a manner rigidly supporting the support arm 20 in a substantially upright orientation. The interaction between the arcuate coupling portion 60 of the support arm 20 and the upper support arm receiving hole 52 and the lower support arm receiving hole 54 is such that pressure is applied at each of the upper and lower support arm receiving holes 52, 54 which causes the support arm 20 to stand in an upright orientation.

Figure 2:
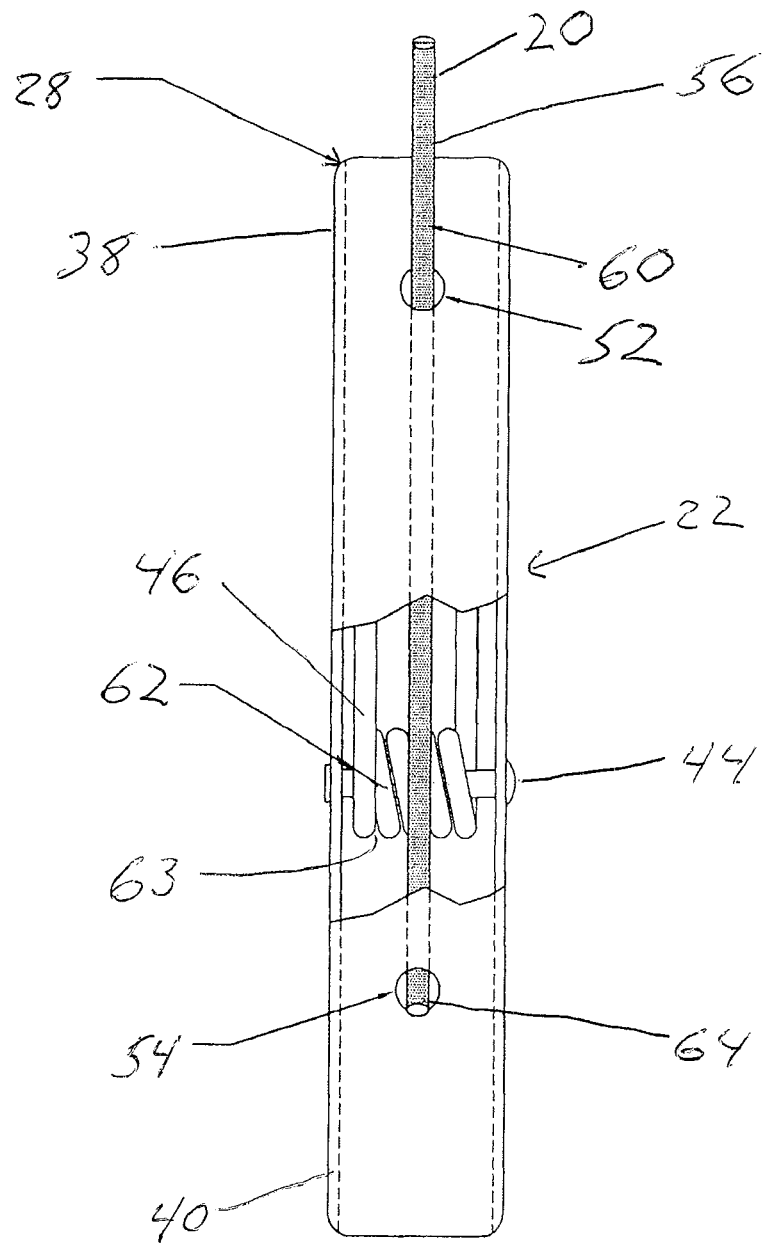
FIG. 2 is a side view of the C-clamp.

In particular, and with reference to FIGS. 1 and 2, the clamp 22 receives and supports the support arm 20 and the hose engaging portion 66 with the first end 56 of the support arm 20, that is, the arcuate coupling portion 60 thereof, passing through the upper support arm receiving hole 52 in the second clamp member 28 and over the spring 46 of the clamp 22, the coils 62 of the spring 46, and terminating with the distal tip 64 of the arcuate coupling portion 60 positioned within the lower support arm receiving hole 54.

Controlled pivotal movement of the support arm 20 and the hose engaging portion 66 relative to the clamp 22 is achieved by allowing for limited interaction between the first end 56 of the support arm 20 and the coils 62 of the spring 46. In particular, the arcuate coupling portion 60 is shaped and dimensioned to seat under pressure within the recesses 63 defined by the coils 62 of the spring 46. In this way, the arcuate coupling portion 60 is held in position relative to the clamp 22 as it sits within one of the recesses 63 defined by the coils 62 of the spring 46. When sufficient lateral pressure is applied to the support arm 20 overcoming the pressure between the arcuate coupling 60 and recess defined by coils 62, a hosing engaging portion 66 is moved, the arcuate coupling portion 60 travels until it moves out of one recess 63 and into the recess adjacent thereto.

Figure 3:
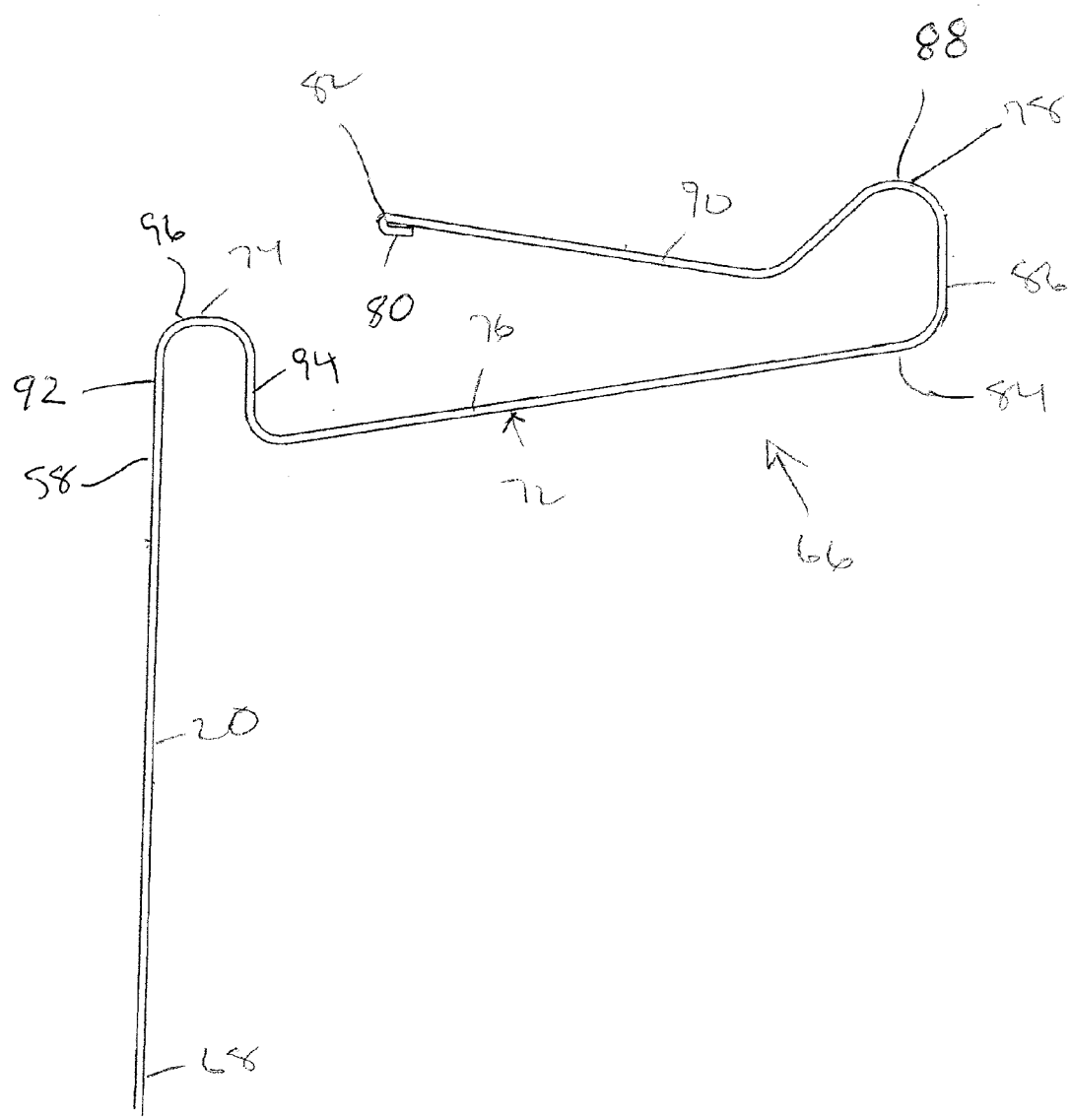
FIG. 3 is front view of the CPAP hose tender.
Figure 4:
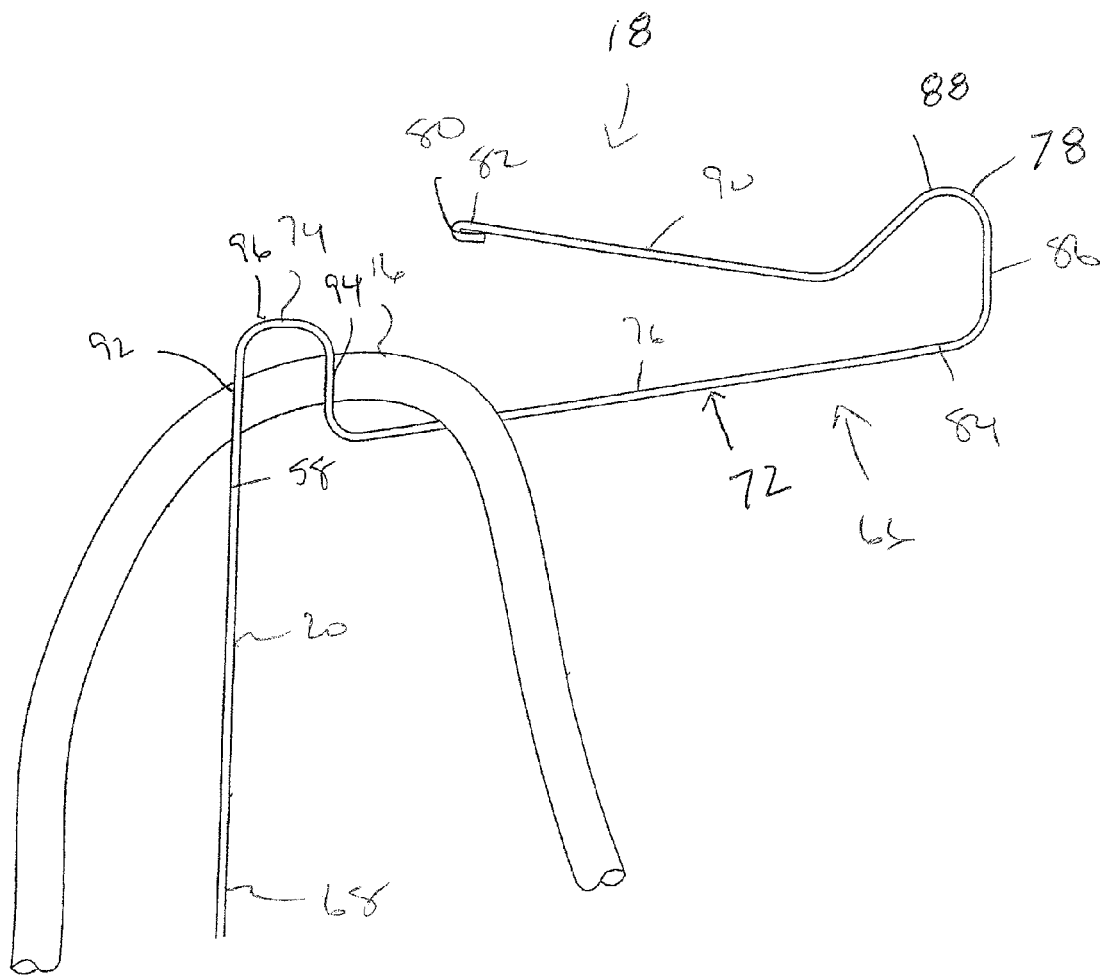
FIG. 4 is a view of an air hose passing through the hose tender.

Referring now to FIGS. 3 and 4, the air hose engaging portion 66 secured to the second end 58 of the support arm 20 is show in detail. The hose engaging portion 66 is secured to, and formed integrally with the support arm 20 (in accordance with a preferred embodiment) and extends transversely thereto for positioning over a patient when the clamp 22 is secured to the headboard 24 of a bed 98. The support arm 20, therefore, includes an elongated upright connecting member 68 extending between the first end 56 of the support arm 20 and the second end 58 of the support arm 20.

The hose engaging portion 66 includes a cantilevered section 72 which is secured to the second end 58 of the support arm 20 and is oriented substantially perpendicular thereto. The cantilevered section 72 includes an abutment member 74 in the form of a 180-degree turn at the connection of the second end 58 of the support arm 20 to the cantilevered section 72. The abutment member 74 includes a vertically oriented first leg 92 connected directly to the second end 58 of the support arm 20. The abutment member 74 further includes a vertically oriented second leg 94 and a connecting member 96 extending between the vertically oriented first leg 92 and the vertically oriented second leg 94. As will be appreciated based upon the following disclosure, the vertically oriented first leg 92 functions as a connection point between the cantilevered section 72 and the second end 58 of the support arm 20, while the vertically oriented second leg 94 is shaped, dimensioned and position for interaction with a air hose 16 hanging upon the cantilevered section 72.

The horizontal line member 76, which defines the primary support surface for the air hose 16, is connected to the end of the vertically oriented second leg 94. The horizontal line member 76 sits vertically beneath the connecting member 96 of the abutment member 74, thereby allowing for the use of the vertically oriented second leg 94 as an abutment surface for lateral movement of the air hose as the air hose 16 sits upon the horizontal line member 76.

The horizontal line member 76 extends between the abutment member 74 to a return portion 78 of the cantilevered section 72. As such, the horizontal line member 76 defines a substantially horizontal support surface upon which an air hose 16 is mounted for support thereof above a patient in a convenient and safe manner. In accordance with a preferred embodiment of the present invention, the horizontal line member 76 is oriented at a substantially transverse, or perpendicular, relative to the longitudinal axis of the support arm 20 and extends a length of approximately 11 inches from the abutment member 74.

The return portion 78 of the cantilevered section 72 defines the termination of the cantilevered section 72 when it ends at a 180-degree bend 80 at the free end 82 at the second end 58 of the support arm 20. The return portion 78 of the cantilevered section 72 includes a first member 84 aligned with and extending from the horizontal line member 76, a second member 86 oriented approximately perpendicular relative to the first member 84, an arcuate third member 88 that completes the return created by the return portion 78. The return portion 78 finishes with a return arm 90 that extends generally horizontally from the third member 88 connected to the return portion 78. In addition to the second member 86 providing a lateral limit for an air hose moving along the horizontal line member 76, the third member 88 and the return arm 90 provide a support surface upon which a user may place the breathing mask 12 for convenient storage thereof during non-use.

Referring now to FIGS. 1 and 4, a view of an air hose 16 passing through the hose tender 18 to the face mask 12 in a manner conveniently and safely supporting the air hose 16 above a patient lying in the bed 98. More particularly, and with the present hose tender 18 secured to the headboard 24 of a bed 98 with the cantilevered section 72 extending substantially parallel to the long axis of the bed 98 and in alignment with the head of a patient sleeping in the bed 98, the air hose 16 extends from the CPAC air generator 14 upwardly adjacent to the support arm 20. As the air hose reaches the air hose engaging portion 66 it is wrapped about the abutment member 74 and passed over the horizontal line member 76. The air hose 16 is wrapped about the abutment member 74 such that it laterally abuts the vertically oriented second leg 94 and is horizontally supported by the horizontal line member 76. The remainder of the air hose 16 extends downwardly to the breathing mask 12 with limited slack in the hose preventing entanglement with the patient.

With the air hose 16 oriented in this manner, the patient is prevented from entanglement with the air hose 16 and the air hose 16 is reliably support above the patient. Even if the user moves while sleeping, the air hose 16 is held in a desired orientation. In particular, the vertically oriented second leg 94 and the second member 86 of the return portion 78 limit movement of the air hose 16 along the longitudinal axis L of the bed 98. In addition, the limited pivotal movement of the support arm 20 offered by the interaction between the coils 62 of the spring 46 and the arcuate coupling portion 60 allow for limited and controlled pivotal movement of the support arm 20 and the hose engaging portion 66 in the event the air hose 16 and breathing mask 12 are moved laterally relative to the longitudinal axis L of the bed 98 as the patient moves while sleeping.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A hose tender for use with a CPAP system, wherein the CPAP system includes a breathing mask connected to an CPAP air generator via a hose, and the hose tender supports the hose above a user in a convenient and safe manner, comprising:
    a support arm including a first end and second end, the first end of the support arm is provided with an arcuate coupling portion and the second end is provided with a hose engaging portion;
    the hose engaging portion includes a cantilevered section secured to the second end of the support arm such that a longitudinal axis of the cantilevered section is oriented substantially perpendicular to a longitudinal axis of the support arm;
    a clamp for selectively securing the support arm to a support surface, the clamp includes an upper support arm receiving hole and a lower support arm receiving hole and the arcuate coupling portion is shaped and dimensioned to simultaneously extend through both the upper support arm receiving hole and the lower support arm receiving hole, and the clamp further includes a spring having coils and the arcuate coupling portion of the support arm is shaped and dimensioned to seat under pressure within recesses defined by the coils of the spring.

2. The hose tender according to claim 1, wherein the clamp includes a first clamp member and a second clamp member, and the first clamp member and the second clamp member are pivotally connected at central pivot point which substantially bisects each of the first clamp member and the second clamp member.

3. The hose tender according to claim 2, wherein the first clamp member includes a first clamp member upper portion and a first clamp member lower portion with a pivot protrusion extending laterally along a length of the first clamp member, and the second clamp member includes a second clamp member upper portion and a second clamp member lower portion with a pivot protrusion extending laterally along a length of the second clamp member.

4. The hose tender according to claim 3, wherein the spring is coupled to the first clamp member and the second clamp member adjacent a pivot pin for biasing the clamp to a closed orientation where the first clamp member lower portion and the second clamp member lower portion are biased toward each other and the first clamp member upper portion and the second clamp member upper portion are biased away from each other.

5. The hose tender according to claim 3, wherein the second clamp member upper portion includes the upper support arm receiving hole and the second clamp member lower portion includes the lower support arm receiving hole.

6. The hose tender according to claim 5, wherein the lower support arm receiving hole and the upper support arm receiving hole are oriented to extended substantially transversely to a longitudinal axis of the second clamp member.

7. The hose tender according to claim 1, wherein the cantilevered section includes an abutment member and a return portion with a horizontal line member connected therebetween.

8. The hose tender according to claim 7, wherein the abutment member is a 180-degree turn at a connection of the support arm to the cantilevered section and includes a vertically oriented first leg connected directly to the support arm, a vertically oriented second leg and a connecting member extending between the vertically oriented first leg and the vertically oriented second leg.

9. The hose tender according to claim 7, wherein the return portion of the cantilevered section includes a first member aligned with and extending from the horizontal line member, a second member oriented substantially perpendicular to the first member, and an arcuate third member that completes the return created by the return portion.

10. The hose tender according to claim 9, wherein the return portion further includes a return arm that extends from the arcuate third member.

11. A hose tender for use with a CPAP system, wherein the CPAP system includes a breathing mask connected to a CPAP air generator via a hose, and the hose tender supports the hose above a user in a convenient and safe manner, comprising:
    a support arm including a first end and second end, the first end of the support arm is provided with an arcuate coupling portion and the second end is provided with a hose engaging portion;
    the hose engaging portion includes a cantilevered section secured to the second end of the support arm such that a longitudinal axis of the cantilevered section is oriented substantially perpendicular to a longitudinal axis of the support arm; wherein the cantilevered section includes an abutment member and a return portion with an horizontal line member connected therebetween;
    a clamp for selectively securing the support arm to a support surface, the clamp includes an upper support arm receiving hole and a lower support arm receiving hole and the arcuate coupling portion is shaped and dimensioned to simultaneously extend through both the upper support arm receiving hole and the lower support arm receiving hole, and the clamp further includes a spring having coils and the arcuate coupling portion of the support arm is shaped and dimensioned to seat within recesses defined by the coils of the spring.

12. The hose tender according to claim 11, wherein the clamp includes a first clamp member and a second clamp member, and the first clamp member and the second clamp member are pivotally connected at central pivot point which substantially bisects each of the first clamp member and the second clamp member.

13. The hose tender according to claim 12, wherein the first clamp member includes a first clamp member upper portion and a first clamp member lower portion with a pivot protrusion extending laterally along a length of the first clamp member, and the second clamp member includes a second clamp member upper portion and a second clamp member lower portion with a pivot protrusion extending laterally along a length of the second clamp member.

14. The hose tender according to claim 13, wherein the spring is coupled to the first clamp member and the second clamp member adjacent a pivot pin for biasing the clamp to a closed orientation where the first clamp member lower portion and the second clamp member lower portion are biased toward each other and the first clamp member upper portion and the second clamp member upper portion are biased away from each other.

15. The hose tender according to claim 13, wherein the second clamp member upper portion includes the upper support arm receiving hole and the second clamp member lower portion includes the lower support arm receiving hole.

16. The hose tender according to claim 15, wherein the lower support arm receiving hole and the upper support arm receiving hole are oriented to extended substantially transversely to a longitudinal axis of the second clamp member.

17. The hose tender according to claim 11, wherein the abutment member is a 180-degree turn at a connection of the support arm to the cantilevered section.

18. The hose tender according to claim 11, wherein the abutment member includes a vertically oriented first leg connected directly to the support arm, a vertically oriented second leg and a connecting member extending between the vertically oriented first leg and the vertically oriented second leg.

19. The hose tender according to claim 11, wherein the return portion of the cantilevered section includes a first member aligned with and extending from the horizontal line member, a second member oriented substantially perpendicular to the first member, and an arcuate third member that completes the return created by the return portion.

20. The hose tender according to claim 19, wherein the return portion further includes a return arm that extends from the arcuate third member.

* * * * *